US00PP16024P2

(12) United States Plant Patent
van Geest

(10) Patent No.: US PP16,024 P2
(45) Date of Patent: Oct. 4, 2005

(54) ***FICUS* PLANT NAMED 'MARGARITA'**

(50) Latin Name: *Ficus benjamina*
Varietal Denomination: Margarita

(75) Inventor: Jan van Geest, s'Gravenzande (NL)

(73) Assignee: Plantenkwekerij J. Van Geest, B.V., s'Gravenzande (NL)

( * ) Notice: Subject to any disclaimer, the term of this patent is extended or adjusted under 35 U.S.C. 154(b) by 28 days.

(21) Appl. No.: 10/806,238

(22) Filed: Mar. 23, 2004

(51) Int. Cl.[7] ..... A01H 5/00
(52) U.S. Cl. ..... Plt./211
(58) Field of Search ..... Plt./211

*Primary Examiner*—Louanne Krawczewicz Myers
(74) *Attorney, Agent, or Firm*—Foley & Lardner, LLP

(57) ABSTRACT

A new and distinct cultivar of *Ficus* plant named 'Margarita', as described and illustrated, and particularly characterized by the variegated yellow-green (lime colored) foliage with a dark green amorphous, irregularly shaped and irregularly patterned spot, located along the midrib of the leaf; and by a heavily branching, upright growth habit.

2 Drawing Sheets

Latin name of the genus and species of the plant claimed: *Ficus benjamina*.
Variety denomination: 'Margarita'.

BACKGROUND OF THE INVENTION

The present invention relates to a new and distinct cultivar of *Ficus benjamina*. The varietal denomination of the new cultivar is 'Margarita'. The new variety was discovered as a naturally occurring spontaneous whole plant mutation in a controlled planting of *Ficus benjamina* 'Midnight' in a greenhouse in s'Gravenzande, The Netherlands in March, 2001.

SUMMARY OF THE INVENTION

The new variety is a naturally occurring spontaneous whole plant mutation of the *Ficus* variety 'Midnight' (U.S. Plant Pat. No. 9,856), and was selected by the inventor, Jan van Geest. The mutation was selected as a single plant among plants of 'Midnight' which were grown in a controlled environment in a glasshouse in s'Gravenzande, The Netherlands in March, 2001. The new variety was first asexually propagated by vegetative cutting in April 2001, in s'Gravenzande, The Netherlands. Asexual reproduction through succeeding generations has established that the combination of characteristics as herein disclosed for the new cultivar are firmly fixed and retained through successive generations of asexual reproduction.

In comparison to the parent plant, 'Midnight', the leaves of 'Margarita' are variegated, yellow-green (lime colored) (near RHS 145A, new foliage, upper side) with a dark green amorphous, irregularly shaped and irregularly patterned (RHS 139B) spot located along the midrib of the leaf. The leaves of 'Midnight' by comparison are 137B (new foliage, upper side). In addition, 'Margarita' varies from the parent plant in leaf and petiole size. The leaves of 'Margarita' are narrower, 3.5 cm, as compared to 4 cm leaf width of 'Midnight', and shorter, 9 cm, as compared to 11 cm long leaves of 'Midnight'. The petioles of 'Margarita' are shorter, approximately 10 mm in length, as compared to 18 mm long petioles of 'Midnight'.

BRIEF DESCRIPTION OF THE INVENTION

The following traits have been repeatedly observed and are determined to be basic characteristics of 'Margarita' which in combination distinguish this *Ficus* as a new and distinct cultivar from parent cultivar 'Midnight' and other *Ficus* cultivars:

1. Variegated colored leaves, having a lime colored leaf with a dark green spot;
2. Irregularly shaped leaves;
3. Irregular patterned spots of very dark green located along the midrib of the leaf; and
4. Heavily branching, upright growth habit.

BRIEF DESCRIPTION OF THE DRAWINGS

The accompanying photographic drawings illustrate the overall appearance of the new *Ficus* cultivar, showing colors as true as is reasonably possible with color reproductions of this type.

The first photographic drawing shows the typical characteristics of *Ficus* 'Margarita' in its entirety.

The second photographic drawing is a close up of the foliage of 'Margarita'.

DETAILED DESCRIPTION OF THE NEW VARIETY

'Margarita' has not been observed under all possible environmental conditions. The phenotypic expression may vary with variations in environment such as temperature, light intensity, day length and cultural conditions, without a change in the genotype of the plant.

The following observations and descriptions are of a 6 month old plant grown in Homestead, Fla. in an unheated, open air shade house from January, 2003 until July, 2003. The shade cloth on the structure has a 73% shade factor. In this description, color references are to The Royal Horticultural Society Colour Chart (R.H.S.). Colors in the photographs may differ slightly from the color values cited in the detailed botanical description which accurately describe the colors of the new *Ficus*. Colors may vary depending upon the degree of horticultural practices such as light level and fertilization techniques.

PLANT

Form: Medium compact, upwardly branching, ascending regularly and richly branching, somewhat weeping.

Growth: Lateral branches are approximately at a 30 to 45 degree angle to the trunk, but slightly weeping at top.

Growth habit: Heavily branching, upright.

Height attained: Vigorous, about 1 meter.

Plant spread/width: 60 cm.

Foliage:

*Size.*—About 3.5 cm wide by about 9 cm long (to leaf tip).

*Quantity.*—Multiple, numerous, exhibits 10–15 leaves on a lateral branch of approximately 15 centimeters.

*Color.*—New foliage: Upper side: Yellow-green, near RHS 145 A with a green spot along the midrib, near RHS 139 B; underside: Yellow-green, near RHS 145 A, with a green spot along the midrib, near RHS 139 C. Old foliage: Upper side: Yellow-green, near RHS 144 A, with a green spot along the midrib, near RHS 139 A; Underside: Yellow-green, near RHS 144 B, with a green spot along the midrib near RHS 137 C.

*Shape.*—Ovate with acuminate leaf tip, slightly coarsely sinuate and glabrous.

*Texture.*—Smooth, leathery, glossy; underside smooth, matte.

*Venation.*—Single mid-rib vein running from petiole to leaf tip, convex on the underside, light green, near RHS 145 B, color is consistent on both upper and lower surfaces of the leaf.

*Edge.*—Smooth, slightly undulated.

*Serration.*—None.

*Stipules.*—Leaves are glabrous.

*Auricle.*—Absent.

*Petiole.*—Near RHS 144 A; about 10 mm long, diameter less than 1 mm and texture smooth.

*Resistance to disease.*—No observations made.

*Rachis.*—None.

Lateral branches: Length, width and internode spacing can vary depending on environmental factors such as light, temperature and nutritional levels of the plant. The description below is from a plant grown in Homestead, Fla. in January of 2005 under shade cloth with 83% shade factor.

*Length.*—12–27 cm.

*Diameter.*—Approximately 4 mm at base of lateral branch to less than one mm at the tip of branch and typical *Ficus benjamina.*

*Internode length.*—15–25 mm.

*Texture.*—Texture of wood is mildly rough and typical of *Ficus benjamina*. Strength of branching is typical of *Ficus benjamina* with medium strength and flexibility capable of supporting weight up to 5 kilos that will bend under that weight nearly reaching the floor.

*Color.*—Grey-brown close to RHS color 199A.

Lenticels: Numerous and evident along the branches and are contrasting in color to the wood as they are a yellow-white color typical of *Ficus benjamina*, near 158D.

*Shape.*—Round and are less than 1 mm in size, typical of *Ficus benjamina.*

Flower/fruit description: Flowers and fruit have not been observed on the plants of the new *Ficus.*

Temperature range: Temperature range relates to an acceptable temperature that the plant can exist under before experiencing irreversible foliage damage and/or death. In this instance, the *Ficus benjamina* 'Margarita' can withstand temperatures as low as 2 degrees Celcius before exhibiting irreversible damage and/or death. It is a tropical plant and will tolerate temperatures typical of other *Ficus benjamina* varieties. No claim is made to the contrary of *Ficus benjamina* tolerances.

*Preferred growing conditions.*—20° C. to 32° C.

Reproductive organs: None observed.

I claim:

1. A new and distinct variety of *Ficus* plant designated 'Margarita', substantially as illustrated and described herein.

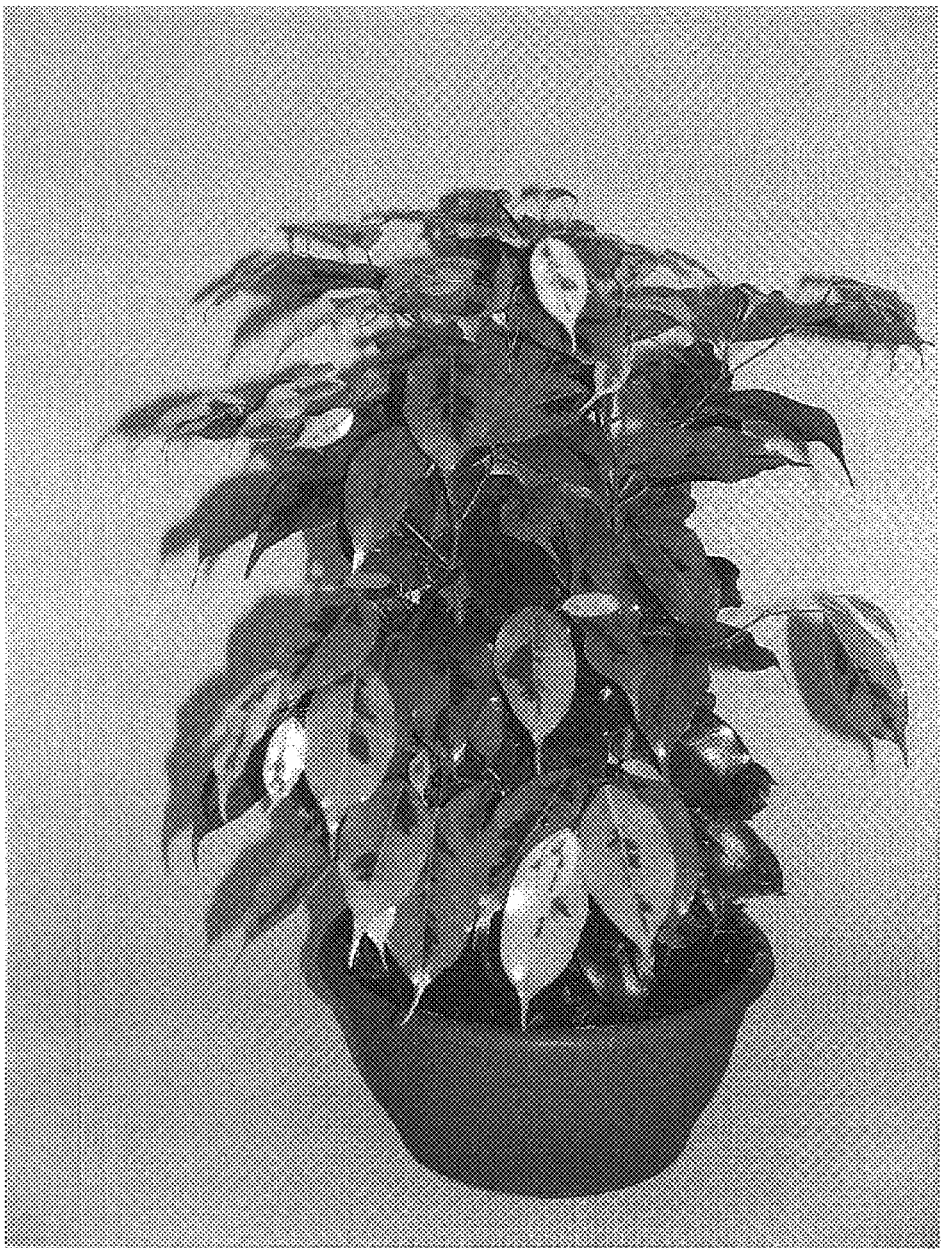

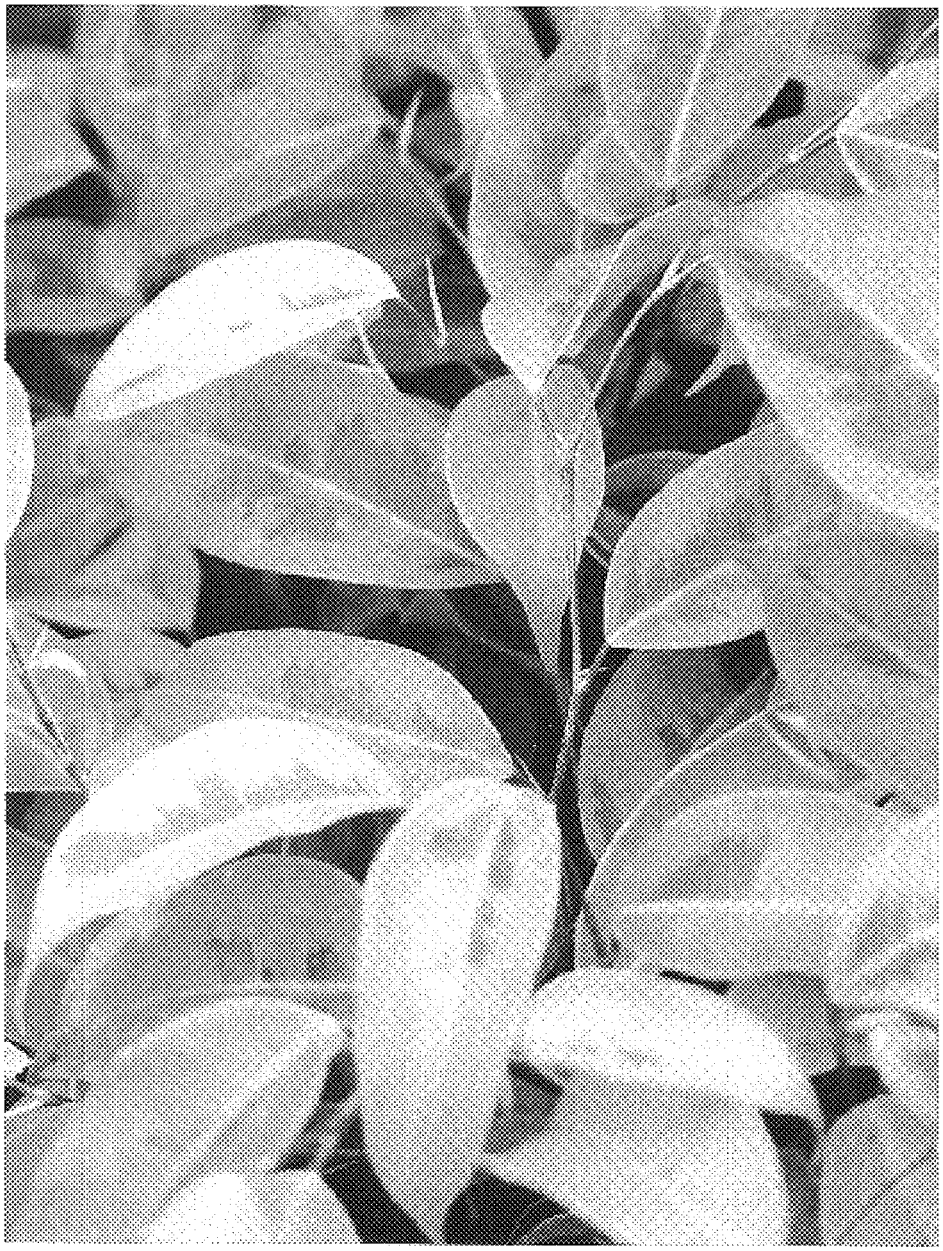

* * * * *